(12) United States Patent
Weber et al.

(10) Patent No.: US 6,430,525 B1
(45) Date of Patent: Aug. 6, 2002

(54) VARIABLE MODE AVERAGER

(75) Inventors: Walter M. Weber, Laguna Hills; Ammar Al-Ali, Tustin, both of CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 09/586,845

(22) Filed: Jun. 5, 2000

(51) Int. Cl.$^7$ .................................... H03H 17/00
(52) U.S. Cl. ........................... 702/194; 702/191
(58) Field of Search .......................... 702/189, 190, 702/191, 193, 194, 195–197, 199

(56) References Cited

U.S. PATENT DOCUMENTS

| | | | |
|---|---|---|---|
| 5,018,088 A | * 5/1991 | Higbie | 702/194 |
| 5,056,052 A | * 10/1991 | Wick et al. | 702/194 |
| 5,511,042 A | * 4/1996 | O'Brien, Jr. | 367/135 |
| 5,632,272 A | 5/1997 | Diab et al. | |
| 5,758,644 A | 6/1998 | Diab et al. | |
| 5,769,785 A | 6/1998 | Diab et al. | |
| 5,782,757 A | 7/1998 | Diab et al. | |
| 6,002,952 A | 12/1999 | Diab et al. | |
| 6,041,290 A | * 3/2000 | Matt et al. | 702/191 |
| 6,094,627 A | * 7/2000 | Peck et al. | 702/199 |

* cited by examiner

*Primary Examiner*—Marc S. Hoff
*Assistant Examiner*—C Steven Miller
(74) *Attorney, Agent, or Firm*—Knobbe, Martens, Olson & Bear, LLP (57) ABSTRACT

A signal processor generates an estimate of a block of weighted input values. An adjustable mode parameter determines a time point relative to the input values at which the estimate is computed. By varying the mode parameter, the output characteristics of the processor are variable between that of a smoother, a filter and a forward predictor of the input values. When input signal confidence is low, the mode parameter is adjusted so that the processor smoothes the input signal. When input signal confidence is high, the mode parameter is adjusted so that the processor output has a faster and more accurate response to the input signal. The variable mode averager is particular applicable to the monitoring of critical physiological parameters in patient-care settings. When applied to pulse oximeter oxygen saturation measurements, the mode parameter can be varied in real-time to achieve a tradeoff between the suppression of false alarms and signal artifacts and the immediate detection of life threatening oxygen desaturation events.

19 Claims, 11 Drawing Sheets

VARIABLE MODE AVERAGER

FIELD OF THE INVENTION

The present invention is directed to the field of signal processing, and, more particularly, is directed to systems and methods for signal averaging.

BACKGROUND OF THE INVENTION

Figure 1:
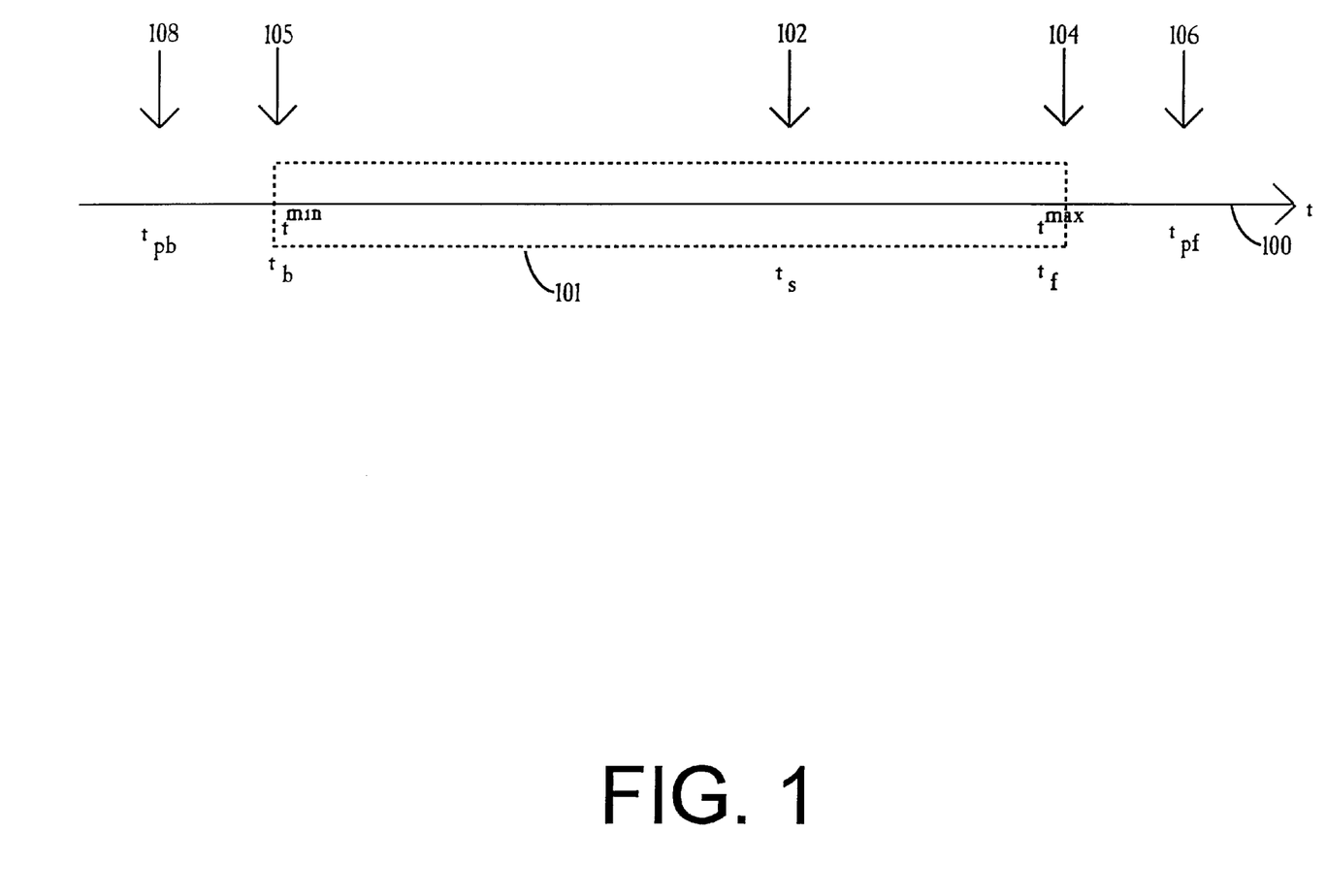
FIG. 1 is a time graph depicting the output of conventional smoother, filter and predictor signal processors.

Digital signal processing techniques are frequently employed to enhance a desired signal in a wide variety of applications, such as health care, communications and avionics, to name a few. Signal enhancement includes smoothing, filtering and prediction. These processing techniques each operate on a block of input signal values in order to estimate the signal at a specific point in time. FIG. 1 illustrates that smoothing, filtering and prediction can be distinguished by the time at which an output value is generated relative to input values. Shown in FIG. 1 is a time axis 100 and a block 101 of input signal values depicted in this example as occurring within a time window between points $t^{min}$ and $t^{max}$. Specifically, the block 101 includes a set of discrete input values $\{v_i; i=1, 2, \ldots n\}$ occurring at a corresponding set of time points $\{t_i; i=1, 2, \ldots n\}$. A smoother operates on the block 101 of input values to estimate the signal at a time point, $t_s$ 102 between $t^{min}$ and $t^{max}$. That is, a smoother generates an output value based upon input values occurring before and after the output value. A filter operates on the block 101 of input values to estimate the signal at a time $t_f$ 104, corresponding to the most recently occurring input value in the block 101. That is, a filter generates a forward filtered output value at the time $t_f$ based upon input values occurring at, and immediately before, the output value. A filter also operates on the block 101 to estimate the signal at a time $t_b$ 105 at the beginning of the block 101 to generate a backward filtered value. A forward predictor operates on the block of input values 101 to estimate the signal at time $t_{pf}$ 106, which is beyond the most recently occurring value in the block 101. That is, a forward predictor generates a forward predicted output value based upon input values occurring prior to the output value. A backward predictor operates on the block 101 of input values to estimate the signal at time $t_{pb}$ 108, which is before the earliest occurring value in the block 101. That is, a backward predictor generates a backward predicted output value based upon input values occurring after the output value.

SUMMARY OF THE INVENTION

A common smoothing technique uses an average to fit a constant, $v^A$, to a set of data values, $\{v_i; i=1, 2, \ldots, n\}$:

$$v^A = \frac{1}{n} \cdot \sum_{i=1}^{n} v_i \tag{1}$$

A generalized form of equation (1) is the weighted average $$v^{WA} = \frac{\sum_{i=1}^{n} w_i \cdot v_i}{\sum_{i=1}^{n} w_i} \tag{2}$$

Here, each value, $v_i$, is scaled by a weight, $w_i$, before averaging. This allows data values to be emphasized and de-emphasized relative to each other. If the data relates to an input signal, for example, values occurring during periods of low signal confidence can be given a lower weight and values occurring during periods of high signal confidence can be given a higher weight.

Figure 2A:
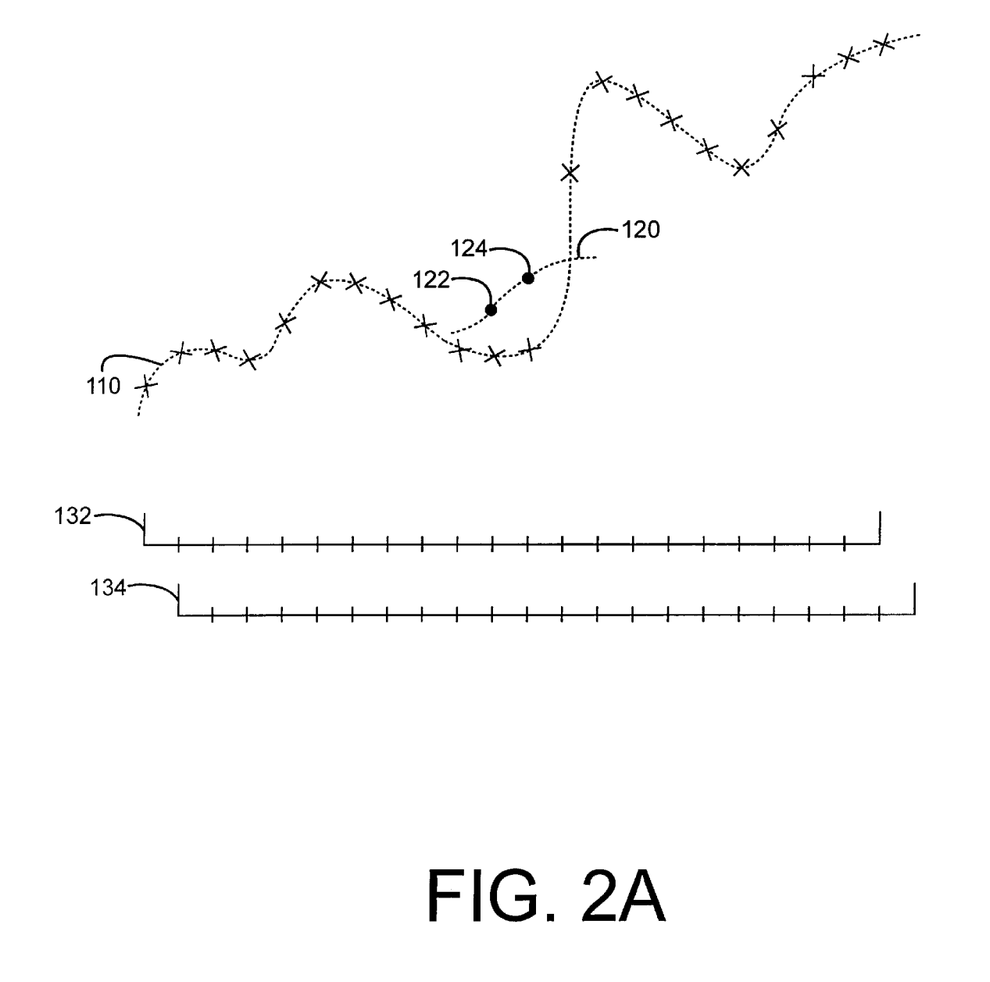
FIG. 2A is an amplitude versus time graph depicting the output of a conventional constant mode averager.

FIG. 2A illustrates the output of a constant mode averager, which utilizes the weighted average of equation (2) to process a discrete input signal, $\{v_i; i \text{ an integer}\}$ 110. The input signal 110 may be, for example, a desired signal corrupted by noise or a signal having superfluous features. The constant mode averager suppresses the noise and unwanted features, as described with respect to FIG. 5, below. A first time-window 132 defines a first set, $\{v_i; i=1, 2, \ldots, n\}$, of signal values, which are averaged together to produce a first output value, $z_1$ 122. A second time-window 134, shifted from the previous window 132, defines a second set $\{v_i; i=2, 3, \ldots, n+1\}$ of signal values, which are also averaged together to produce a second output value $z_2$ 124. In this manner, a discrete output signal, $\{z_j; j \text{ an integer}\}$ 120 is generated from a moving weighted average of a discrete input signal $\{v_i; i \text{ an integer}\}$ 110, where:

$$z_j = \sum_{i=j}^{n+j-1} w_i v_i \Big/ \sum_{i=j}^{n+j-1} w_i \tag{3}$$

Figure 2B:
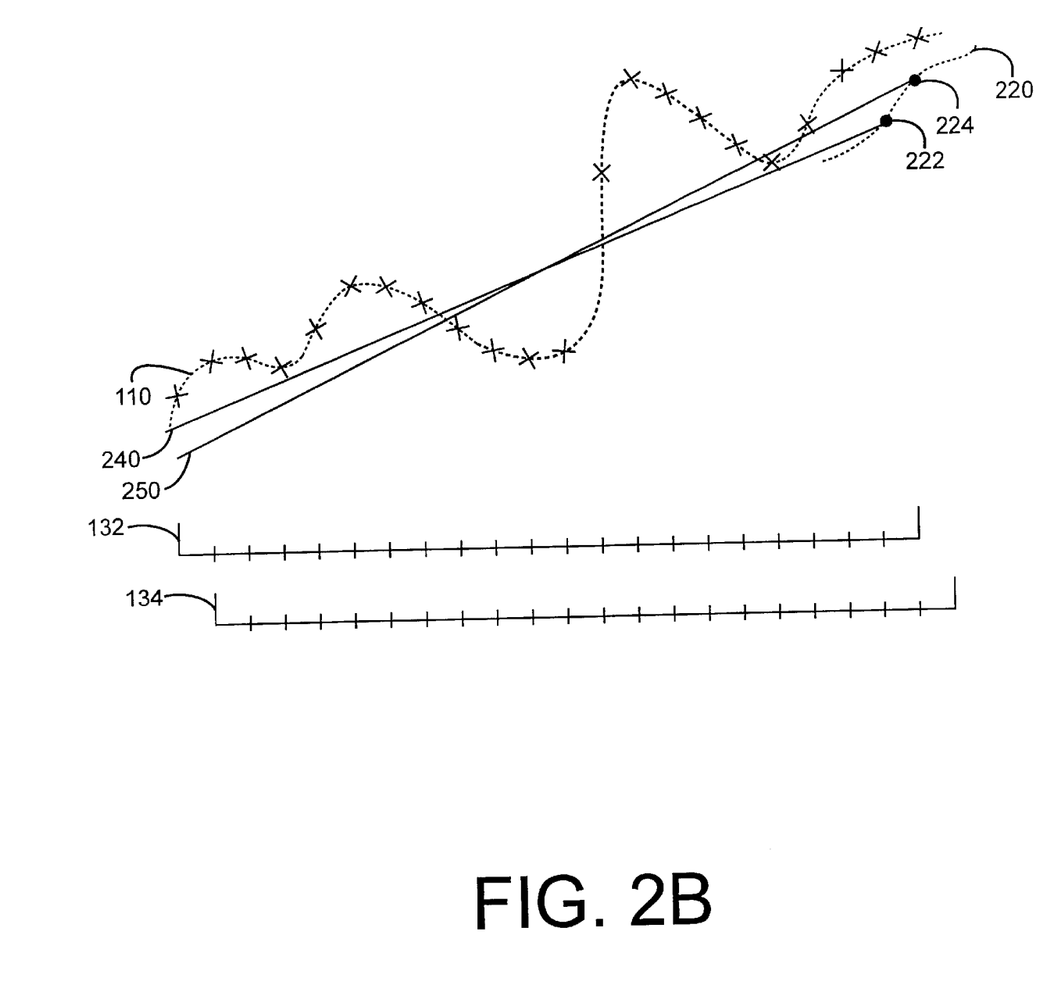
FIG. 2B is an amplitude versus time graph depicting the output of a conventional linear mode averager.

A common filtering technique computes a linear fit to a set of data values, $\{v_i; i=1, 2, \ldots, n\}$:

$$\hat{v}_i = \alpha \cdot t_i + \beta \tag{4}$$

where $\alpha$ and $\beta$ are constants and $t_i$ is the time of occurrence of the $i^{th}$ value. FIG. 2B illustrates the output of a linear mode averager, which uses the linear fit of equation (4) to process a discrete input signal, $\{v_i; i \text{ an integer}\}$ 110. The input signal 110 may be, for example, a desired signal with important features corrupted by noise. The linear mode averager reduces the noise but tracks the important features, as described with respect to FIG. 6 below. A first time-window 132 defines a first set, $\{v_i; i=1, 2, \ldots, n\}$, of signal values. A linear fit to these n values is a first line 240, and the value along this line at max $\{t_1, t_2, \ldots, t_n\}$ is equal to a first output value, $z_1$ 222. A second time-window 134 shifted from the previous window 132 defines a second set, $\{v_i; i=2, 3, \ldots, n+1\}$, of signal values. A linear fit to these n values is a second line 250, and the value along this line at max $\{t_2, t_3, \ldots, t_n+1\}$ is equal to a second output value, $z_2$ 224. In this manner, a discrete output signal, $\{z_j; j \text{ an integer}\}$ 220 is generated from a moving linear fit of a discrete input signal $\{v_i; i \text{ an integer}\}$, where:

$$z_j = \alpha_j \cdot t_{n+j-1}^{MAX} + \beta_j \tag{5a}$$

$$t_{n+j-1}^{MAX} = \max\{t_j, t_{j+1}, \ldots, t_{n+j-1}\} \tag{5b}$$

In general, the time windows shown in FIGS. 2A–2B may be shifted from each other by more than one input value, and values within each time window may be skipped, i.e., not included in the average. Further, the $t_i$'s may not be in increasing or decreasing order or uniformly distributed, and successive time windows may be of different sizes. Also, although the discussion herein refers to signal values as the dependent variable and to time as the independent variable to facilitate disclosure of the present invention, the concepts involved are equally applicable where the variables are other than signal values and time. For example, an independent variable could be a spatial dimension and a dependent variable could be an image value.

The linear mode averager described with respect to FIG. 2B can utilize a "best" linear fit to the input signal, calculated by minimizing the mean-squared error between the linear fit and the input signal. A weighted mean-squared error can be described utilizing equation (4) as:

$$\varepsilon(\alpha, \beta) = \sum_{i=1}^{n} w_i(v_i - \hat{v}_i)^2 / \sum_{i=1}^{n} w_i \qquad (6a)$$

$$\varepsilon(\alpha, \beta) = \sum_{i=1}^{n} w_i[v_i - (\alpha \cdot t_i + \beta)]^2 / \sum_{i=1}^{n} w_i \qquad (6b)$$

Conventionally, the least-mean-squared (LMS) error is calculated by setting the partial derivatives of equation (6b) with respect to $\alpha$ and $\beta$ to zero:

$$\frac{\partial}{\partial \alpha}\varepsilon(\alpha, \beta) = 0 \qquad (7a)$$

$$\frac{\partial}{\partial \beta}\varepsilon(\alpha, \beta) = 0 \qquad (7b)$$

Substituting equation (6b) into equation (7b) and taking the derivative yields:

$$-2\sum_{i=1}^{n} w_i[v_i - (\alpha \cdot t_i + \beta)] / \sum_{i=1}^{n} w_i = 0 \qquad (8)$$

Solving equation (8) for $\beta$ and substituting the expression of equation (2) yields:

$$\beta = \frac{\sum_{i=1}^{n} w_i \cdot v_i}{\sum_{i=1}^{n} w_i} - \alpha \frac{\sum_{i=1}^{n} w_i \cdot t_i}{\sum_{i=1}^{n} w_i} \qquad (9a)$$

$$\beta = v^{WA} - \alpha \cdot t^{WA} \qquad (9b)$$

where the weighted average time, $t^{WA}$, is defined as:

$$t^{WA} = \frac{\sum_{i=1}^{n} w_i \cdot t_i}{\sum_{i=1}^{n} w_i} \qquad (10)$$

Substituting equation (9b) into equation (4) gives:

$$\hat{v}_i = \alpha(t_i - t^{WA}) + v^{WA} \qquad (11)$$

Substituting equation (11) into equation (6a) and rearranging terms results in:

$$\varepsilon(\alpha, \beta) = \sum_{i=1}^{n} w_i[(v_i - v^{WA}) - \alpha \cdot (t_i - t^{WA})]^2 / \sum_{i=1}^{n} w_i \qquad (12)$$

Changing variables in equation (12) gives:

$$\varepsilon(\alpha, \beta) = \sum_{i=1}^{n} w_i(v'_i - \alpha \cdot t'_i)^2 / \sum_{i=1}^{n} w_i \qquad (13)$$

where:

$$v'_i = v_i - v^{WA} \qquad (14a)$$

$$t'_i = t_i - t^{WA} \qquad (14b)$$

Substituting equation (13) into equation (7a) and taking the derivative yields $$-2\sum_{i=1}^{n} w_i t'_i(v'_i - \alpha \cdot t'_i) / \sum_{i=1}^{n} w_i = 0 \qquad (15)$$

Solving equation (15) for $\alpha$ gives:

$$\alpha = \frac{\sum_{i=1}^{n} w_i v'_i t'_i / \sum_{i=1}^{n} w_i}{\sum_{i=1}^{n} w_i t'^2_i / \sum_{i=1}^{n} w_i} \qquad (16)$$

Substituting equations (14a, b) into equation (16) results in:

$$\alpha = \frac{\sum_{i=1}^{n} w_i(v_i - v^{WA})(t_i - t^{WA}) / \sum_{i=1}^{n} w_i}{\sum_{i=1}^{n} w_i(t_i - t^{WA})^2 / \sum_{i=1}^{n} w_i} \qquad (17a)$$

$$\alpha = \frac{\sigma^2_{vt}}{\sigma^2_{tt}} \qquad (17b)$$

where:

$$\sigma^2_{vt} = \sum_{i=1}^{n} w_i(v_i - v^{WA})(t_i - t^{WA}) / \sum_{i=1}^{n} w_i \qquad (18a)$$

$$\sigma^2_{tt} = \sum_{i=1}^{n} w_i(t_i - t^{WA})^2 / \sum_{i=1}^{n} w_i \qquad (18b)$$

Finally, substituting equation (17b) into equation (11) provides the equation for the least-mean-square (LMS) linear fit to $\{v_i; i=1, 2, \ldots, n\}$:

$$\hat{v}_i = \frac{\sigma^2_{vt}}{\sigma^2_{tt}}(t_i - t^{WA}) + v^{WA} \qquad (19)$$

Figure 3:
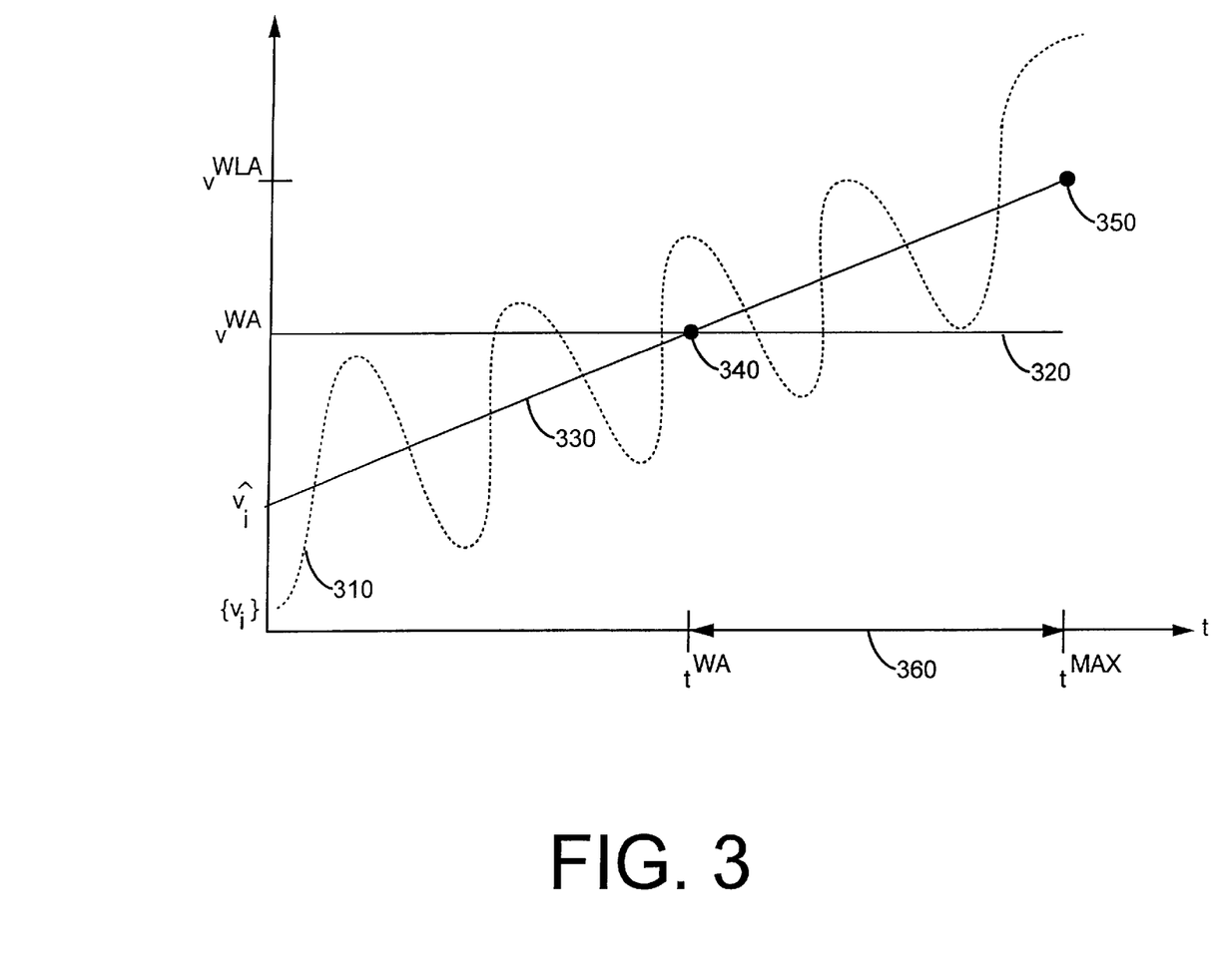
FIG. 3 is an amplitude versus time graph comparing the outputs of a constant mode averager and a linear mode averager.

FIG. 3 provides one comparison between the constant mode averager, described above with respect to FIG. 2A and equation (2), and the linear mode averager, described above with respect to FIG. 2B and equation (19). Shown in FIG. 3 are input signal values $\{v_i; i=1, 2, \ldots, n\}$ 310. The constant mode averager calculates a constant 320 for these values 310, which is equal to $v^{WA}$, the weighted average of the input values $v_i$. Thus, the constant mode averager output 340 has a value $v^{WA}$. For comparison to the linear mode averager, the constant mode averager output can be conceptualized as an estimate of the input values 310 along a linear fit 350, evaluated at time $t^{WA}$. The linear mode averager may be thought of as calculating a LMS linear fit, $\hat{v}_i$ 330 to the input signal values, $v_i$ 310. The linear mode averager output 350 has a value, $v^{WLA}$. The linear mode averager output is an estimate of the input values 310 along the linear fit 330, described by equation (19), evaluated at an index i such that $t_i = t^{MAX}$:

$$v^{WLA} = \frac{\sigma_{vt}^2}{\sigma_{tt}^2}(t^{MAX} - t^{WA}) + v^{WA} \qquad (20)$$

where:

$$t^{MAX} = \max\{t_1, t_2, \ldots, t_n\} \qquad (21)$$

As illustrated by FIG. 3, unlike the constant mode averager, the linear mode averager is sensitive to the input signal trend. That is, the constant mode averager provides a constant fit to the input values, whereas the linear mode averager provides a linear fit to the input values that corresponds to the input value trend. As a result, the output of the linear mode averager output responds faster to changes in the input signal than does the output of the constant mode averager. The time lag or delay between the output of the constant mode averager and the output of the linear mode averager can be visualized by comparing the time difference 360 between the constant mode averager output value 340 and the linear mode averager output value 350.

Figure 4:
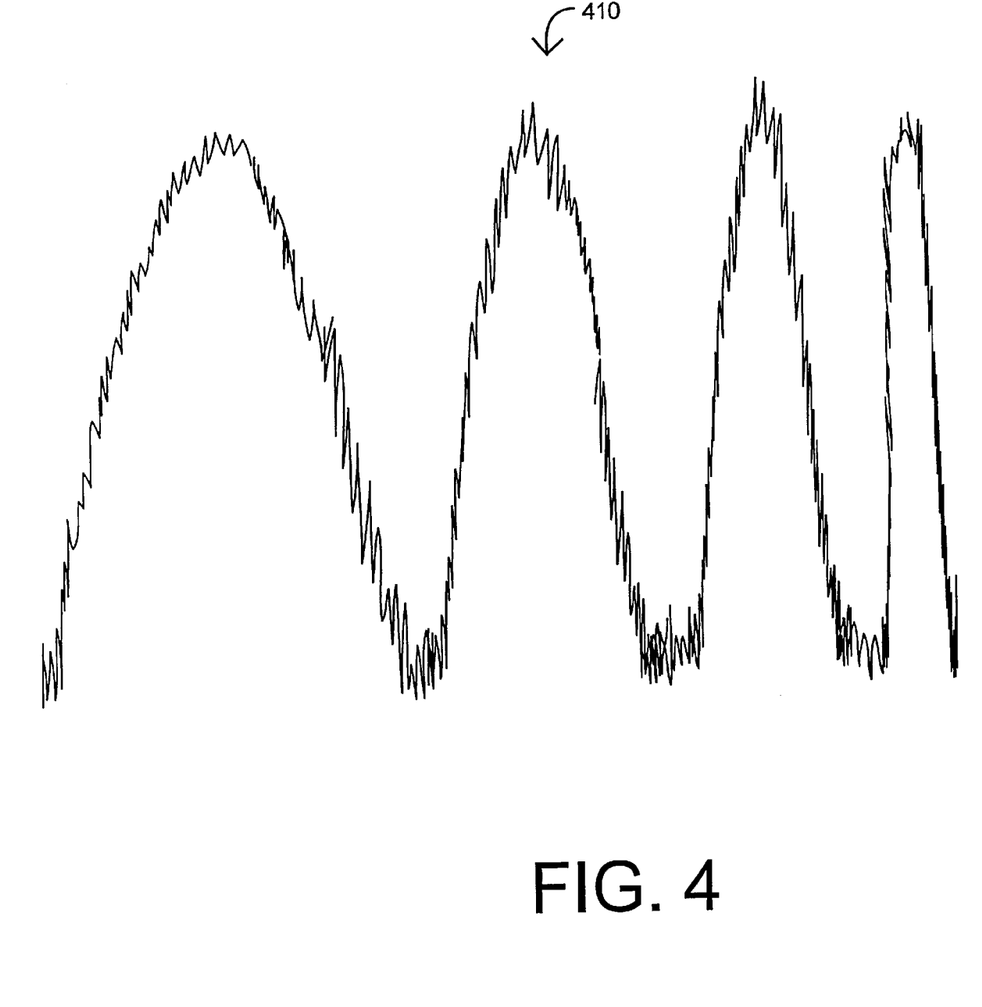
FIG. 4 is an amplitude versus time graph depicting a noisy input signal.
Figure 5:
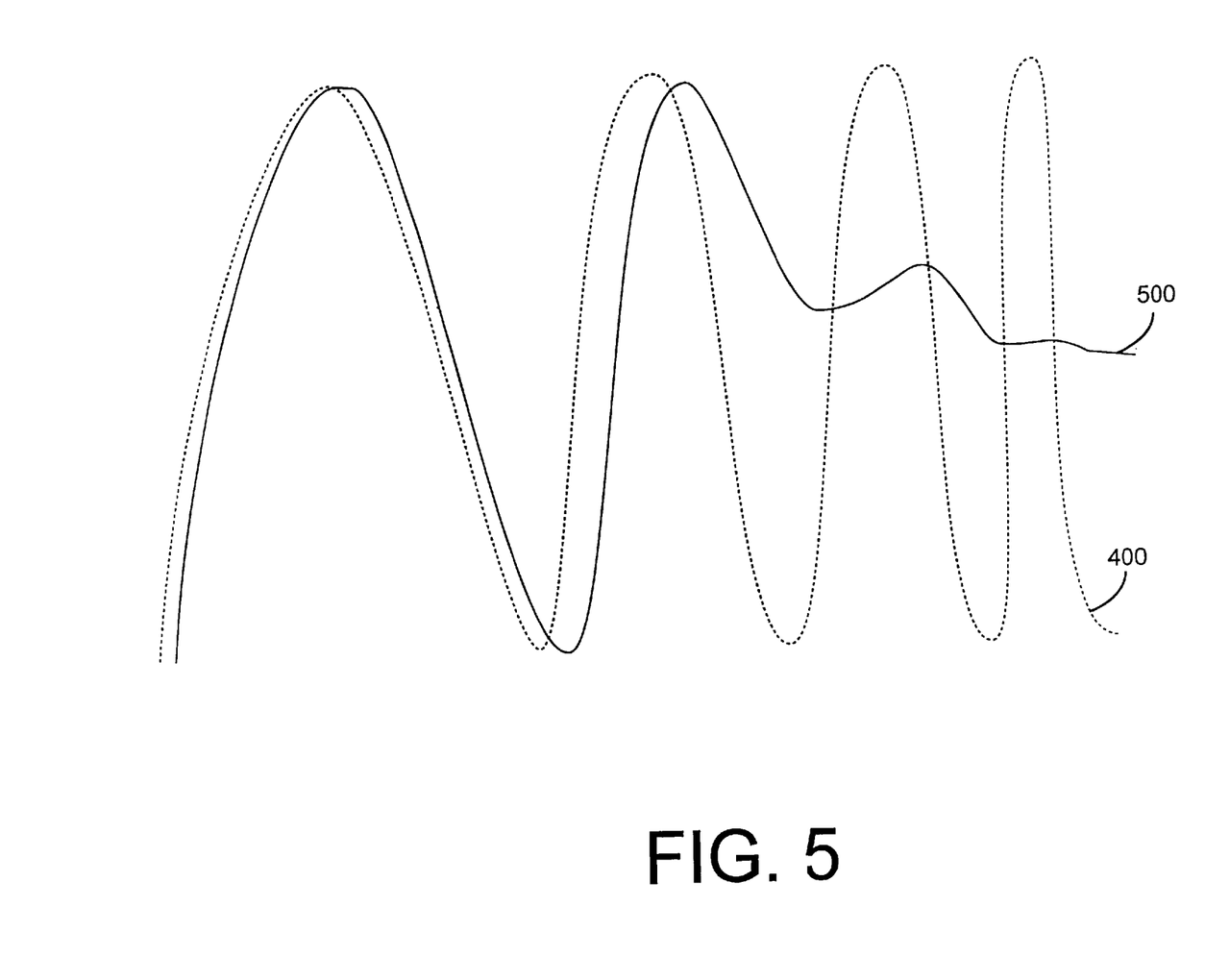
FIG. 5 is an amplitude versus time graph depicting a constant mode averager output signal corresponding to the input signal of FIG. 4.
Figure 6:
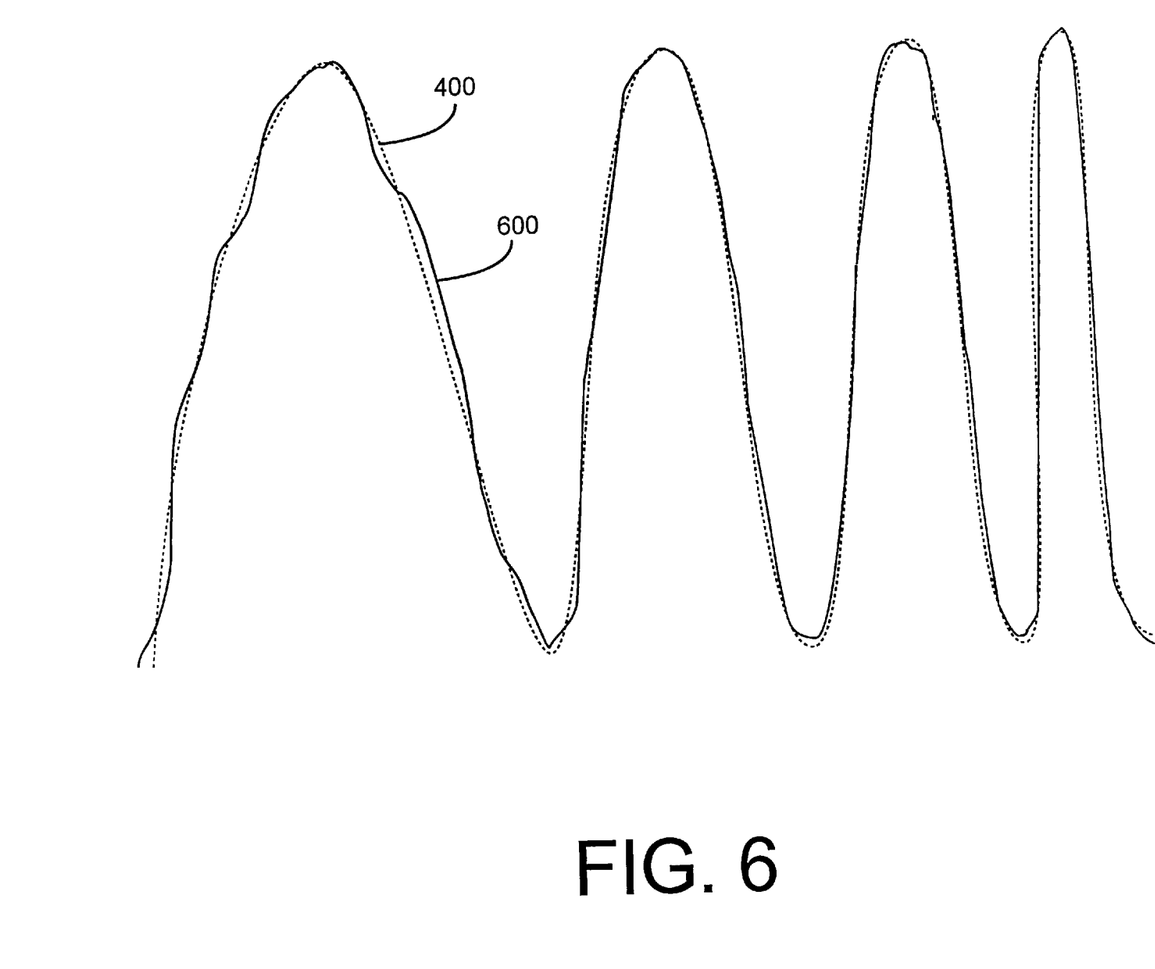
FIG. 6 is an amplitude versus time graph depicting a linear mode averager output signal corresponding to the input signal of FIG. 4.

FIGS. 4–6 illustrate further comparisons between the constant mode averager and the linear mode averager. FIG. 4 depicts a noise-corrupted input signal 410, which increases in frequency with time. FIGS. 5–6 depict the corresponding noise-free signal 400. FIG. 5 also depicts the constant mode averager output 500 in response to the input signal 410, with the noise-free signal 400 shown for reference. FIG. 6 depicts the linear mode averager output 600 in response to the input signal 410, with the noise-free signal 400 also shown for reference. As shown in FIG. 5, the constant mode averager output 500 suppresses noise from the input signal 410 (FIG. 4) but displays increasing time lag and amplitude deviation from the input signal 400 as frequency increases. As shown in FIG. 6, the linear mode averager output 600 tends to track the input signal 400 but also tracks a portion of the noise on the input signal 410.

FIGS. 4–6 suggest that it would be advantageous to have an averager that has variable characteristics between those of the linear mode averager and those of the constant mode averager, depending on signal confidence. Specifically, it would be advantageous to have a variable mode averager that can be adjusted to track input signal features with a minimal output time lag when signal confidence is high and yet adjusted to smooth an input signal when signal confidence is low. Further, it would be advantageous to have a variable mode averager that can be adjusted so as not to track superfluous input signal features regardless of signal confidence.

One aspect of the present invention is a variable mode averager having a buffer that stores weighted input values. A mode input specifies a time value relative to the input values. A processor is coupled to the buffer, and the processor is configured to provide an estimate of the input values that corresponds to the time value. In a particular embodiment, the mode input is adjustable so that the estimate varies between that of a smoother and that of a forward predictor of the input values. In another embodiment, the mode input is adjustable so that the estimate varies between that of a smoother and that of a filter of the input values. In yet another embodiment, the mode input is adjustable so that the estimate varies between that of an average of the input values and that of a filter of the input values. The mode input may be adjustable based upon a characteristic associated with the input values, such as a confidence level. In one variation of that embodiment, the estimate can be that of a smoother when the confidence level is low and that of a filter when the confidence level is high. The estimate may occur along a curve-fit of the input values at the time value. In one embodiment, the curve-fit is a linear LMS fit to the input values.

Another aspect of the present invention is a signal averaging method. The method includes identifying signal values and determining weights corresponding to the signal values. The method also includes computing a trend of the signal values adjusted by the weights. Further, the method includes specifying a time value relative to the signal values based upon a characteristic associated with the signal values and estimating the signal values based upon the trend evaluated at the time value. The method may also incorporate the steps of determining a confidence level associated with the signal values and specifying the time value based upon the confidence level. In one embodiment, the trend is a linear LMS fit to the signal values adjusted by the weights. In that case, the time value may generally correspond to the maximum time of the signal values when the confidence level is high and generally correspond to the weighted average time of the signal values when the confidence level is low.

Yet another aspect of the present invention is a signal averaging method having the steps of providing an input signal, setting a mode between a first mode value and a second mode value and generating an output signal from an estimate of the input signal as a function of said mode. The output signal generally smoothes the input signal when the mode is proximate the first mode value, and the output signal generally tracks the input signal when the mode is proximate the second mode value. The method may also include determining a characteristic of the input signal, where the setting step is a function of the characteristic. In one embodiment, the characteristic is a confidence level relating to the input signal. In another embodiment, the setting step incorporates the substeps of setting the mode proximate the first mode value when the confidence level is low and setting the mode proximate the second mode value when the confidence level is high. In another embodiment, the input signal is a physiological measurement and the setting step comprises setting the mode proximate the first mode value when the measurement is corrupted with noise or signal artifacts and otherwise setting the mode proximate the second mode value so that the output signal has a fast response to physiological events.

A further aspect of the present invention is a signal averager having an input means for storing signal values, an adjustment means for modifying the signal values with corresponding weights, a curve fitting means for determining a trend of the signal values, and an estimate means for generating an output value along the trend. The signal averager may further have a mode means coupled to the estimate means for variably determining a time value at which to generate the output value.

DETAILED DESCRIPTION OF THE PREFERRED EMBODIMENTS

Figure 7:
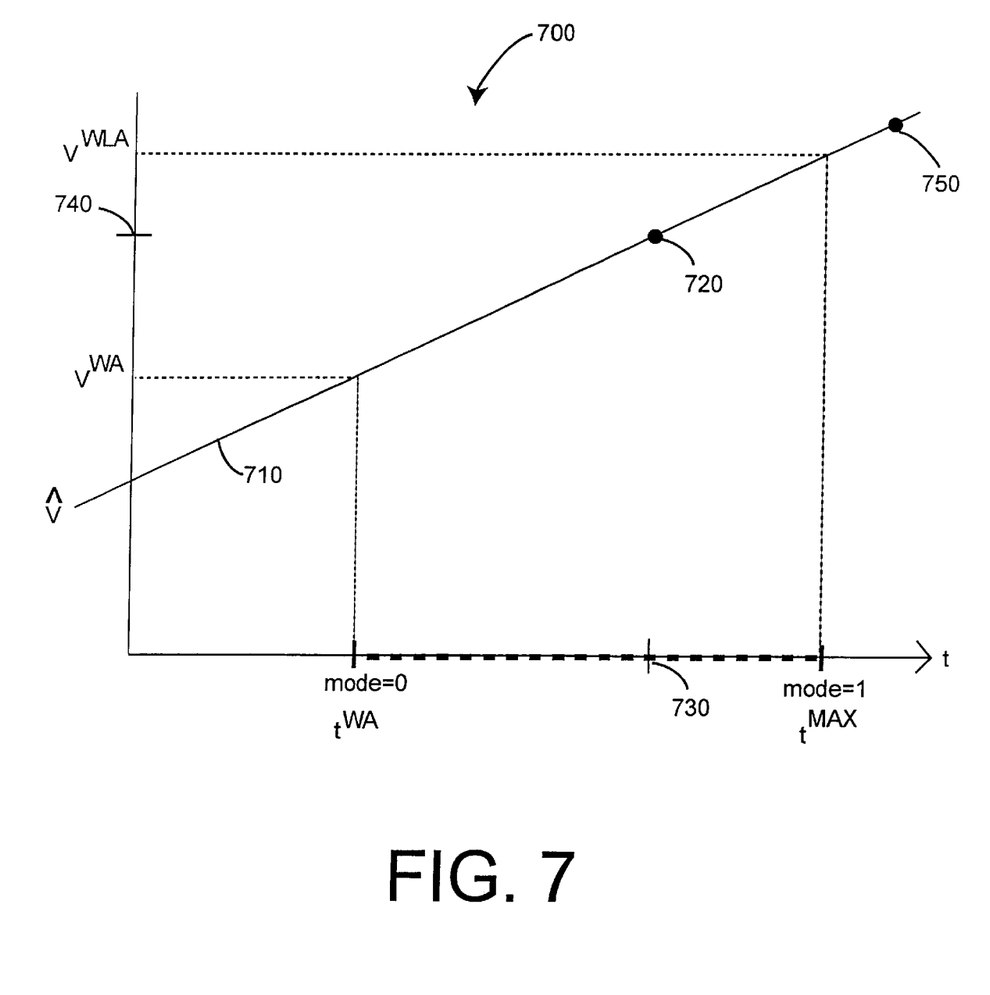
FIG. 7 is an amplitude versus time graph illustrating the characteristics of one embodiment of the variable mode averager.

FIG. 7 illustrates the output characteristics of a variable mode averager according to the present invention. The output of the variable mode averager is a mode-dependent weighted linear average (MWLA) defined as $$v^{MWLA} = mode \cdot \frac{\sigma_{vt}^2}{\sigma_{tt}^2}(t^{MAX} - t^{WA}) + v^{WA} \quad (22)$$

Equation (22) is a modified form of equation (20), which is motivated by equations (2) and (19) along with recognition of the relationships in Table 1.

TABLE 1

VARIABLE MODE AVERAGER OUTPUT

Figure 8:
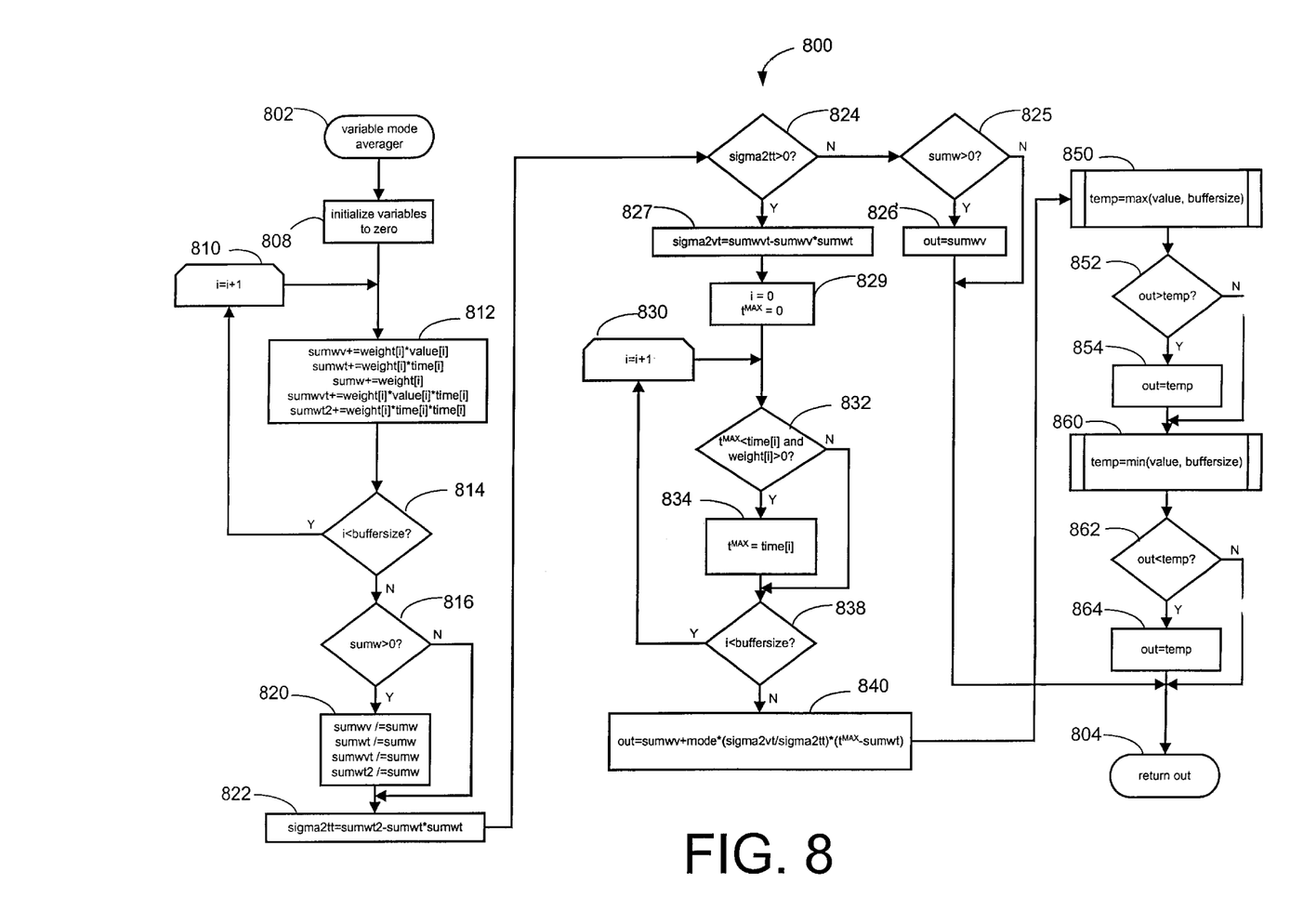
FIG. 8 is a flow chart of a variable mode averager embodiment.

|  | mode = 0 | mode = 1 | any mode ≥ 0 |
| --- | --- | --- | --- |
| Processing Function | Constant Mode Averager | Linear Mode Averager | Variable Mode Averager |
| Output | $v^{WA}$ | $v^{WLA}$ | $v^{MWLA}$ |
| Defining Formula | Equation (2) | Equation (20) | Equation (22) |
| Processing Method | Weighted Average | LMS Linear Fit | Figure 8 |

As shown in Table 1, the Variable Mode Averager in accordance with the present invention includes the constant mode averager processing function and the linear mode averager processing function, which are known processing functions. As farther shown in Table 1, the Variable Mode Averager of the present invention also includes a variable mode averager processing function, which will be described below.

As shown in Table 1, if mode=0, the variable mode averager output is $v^{WA}$, the output of the constant mode averager function, which utilizes a weighted average of the input signal values. If mode=1, the variable mode averager output is $v^{wLA}$, the output of the linear mode averager function, which utilizes a LMS linear fit to the input signal values. If 0<mode<1, then the variable mode averager output is $v^{MWLA}$ and has output characteristics that are between that of the constant mode averager and the linear mode averager. In addition, if mode>1, then the variable mode averager behaves as a forward predictor.

As shown in FIG. 7, the variable mode averager output 720 is an estimate of the input values at a selected time along the linear fit 710, which indicates a trend of the input values. Assuming 0 <mode<1, the mode variable determines the equivalent time 730 between $t^{WA}$ and $t^{MAX}$ for which the estimate is evaluated, yielding an output value 740 between $v^{WA}$ and $v^{WLA}$. Thus, the mode variable acts to parametrically vary the time delay between the input and output signals of the variable mode averager, along with associated output characteristics. If mode=0, the time delay 360 (FIG. 3) is that of the constant mode averager. If mode=1, there is no time delay. If mode>1, the variable mode averager is predicting a future input value based on n past values. In this manner, the variable mode averager can be used to advantageously adjust between the smoothing characteristics of the constant mode averager and the tracking characteristics of the linear mode averager, as described above with respect to FIGS. 4–6. The variable mode control determines how much of each particular characteristic to use for a particular input signal and application. For example, for time periods when the input signal has low confidence, mode can be set further towards zero, although with a time lag penalty. For time periods when the input signal has high confidence or when minimum time lag is required, mode can be set further towards one, or even to a value greater than one.

The variable mode averager has been described in terms of weighted input values. One of ordinary skill, however, will recognize that the present invention includes the case where all of the weights are the same, i.e., where the input values are equally weighted or unweighted. Further, although the variable mode averager has been described in terms of a linear mode averager, one of ordinary skill in the art will recognize that a variable mode averager could also be based on non-linear curve fits, such as exponential or quadratic curves indicating a non-linear trend of the input signal. In addition, one of ordinary skill will understand that the variable mode averager can be implemented to operate on continuous data as well as infinitely long data. Also, a variable mode averager based upon a linear fit by some criteria other than LMS; a variable mode averager using any mode value, including negative values; and a variable mode averager based upon a linear fit where $t^{min}=\min\{t_1, t_2, \ldots, t_n\}$ is substituted for $t^{MAX}$ in equation (22) are all contemplated as within the scope of the present invention.

FIG. 8 illustrates one embodiment 800 of a variable mode signal averager. After an entry point 802, variables are initialized to zero in a block 808. Next, in a block 812, the sums of various parameters are calculated by summing the products of corresponding values in each of three buffers: an input data buffer, value[i]; a weight buffer, weight[i]; and a time value buffer, time[i]. In addition, the weight[i] values are summed. These sums are calculated over the entire length of each buffer, representing a single time window of n values. The calculations are performed by incrementing a loop counter i in a block 810 and reentering the block 812. The loop counter i specifies a particular value in each buffer. Each time through the block 812, the variable mode signal averager generates products of buffer values and adds the results to partial sums. After completing the partial sums, the variable mode signal averager then determines if the ends of the buffers have been reached in a decision block 814 by comparing the incremented value of i to the size of the buffer. If the ends of the buffers have not been reached, the variable mode averager increments the loop counter i and reenters the block 812; otherwise, the variable mode averager continues to a decision block 816.

In the decision block 816, a check is made whether the sum of the weights, sumw, is greater than zero. If so, each of the sums of the products from the block 812 is divided by sumw in a block 820. In the block 820, the parameters computed are:

sumwv, the weighted average value of equation (2);
sumwt, the weighted average time of equation (10);
sumwvt, the weighted average product of value and time; and
sumwt2, the weighted average product of time squared.

The sumwt2 parameter from the block 820 is then used in a block 822 to calculate an autovariance sigma2tt in accordance with equation (18b). If, in a decision block 824, a determination is made that the autovariance is not greater than zero, then in a decision block 825, a determination is made whether the sum of the weights is greater than zero. If, in the decision block 825, the sum of the weights is not greater than zero, then an output value, out, which was initialized to zero in the block 808, is returned as a zero value at a termination point 804. Otherwise, if, in the decision block 825, a determination is made that the sum of the weights is greater than zero, then in a block 826, the value of the sum of the weights is assigned to the output value, out, and the output value is then returned at the termination point 804.

If, in the decision block 824, the autovariance is determined to be greater than zero, then in a block 827, the sumwvt parameter from the block 820 is used to calculate a crossvariance signal sigma2vt in accordance with equation (18a). Thereafter, the maximum time, $t^{MAX}$, as defined in equation (21), is determined by finding the largest time value in the time buffer, time[i]. In particular, in a block 829, the loop counter, i, is reinitialized to zero and the value of $t^{MAX}$ is initialized to zero. Next, in a decision block 832, the current value of $t^{MAX}$ is compared to the current value of the time buffer indexed by the loop counter, i. If the current value of $t^{MAX}$ is not less than the current value of the time buffer or if the current weight value indexed by i is not greater than zero, then $t^{MAX}$ is not changed and a block 834 is bypassed. On the other hand, if the current value of $t^{MAX}$ is less than the current time value and if the current weight value is greater than zero, then the block 834 is entered, and the value of $t^{MAX}$ is replaced with the current time value time[i]. In either case, in a decision block 838, the loop counter, i, is compared to the buffer size, and, if the loop counter, i, is less than the buffer size, the loop counter, i, is incremented in a block 830, and the comparisons are again made in the decision block 832.

When, in the decision block 838, it is determined that the loop counter, i, has reached the buffer size, the variable mode averager proceeds to a block 840 with the largest value of time[i] saved as the value of $t^{MAX}$. In the block 840, a single output value, out, is computed in accordance with equation (22). Thereafter, the output value, out, is limited to the range of values in the input data buffer, value[i]. This is accomplished by comparing out to the maximum and minimum values in the data buffer. First, in a block 850, the maximum of the value buffer is determined. Then, in a decision block 852, the maximum of the value buffer is compared to out. If out is bigger than the maximum of the value buffer, then, in a block 854, out is limited to the maximum value in the buffer. Otherwise, the block 854 is bypassed, and out remains as previously calculated in the block 840. Thereafter, in a block 860, the minimum of the value buffer is determined. The minimum of the value buffer is compared to out in a decision block 862. If out is smaller than the minimum of the value buffer, then, in a block 864, out is set to the minimum value in the buffer. Otherwise, the block 864 is bypassed, and out is not changed. The value of out determined by the block 840, the block 852 or the block 864 is then returned from the routine via the termination point 804.

In one embodiment, the process described with respect to FIG. 8 is implemented as firmware executing on a digital signal processor. One of ordinary skill in the art will recognize that the variable mode averager can also be implemented as a digital circuit. Further, a variable mode averager implemented as an analog circuit with analog inputs and outputs is also contemplated to be within the scope of the present invention.

Pulse oximetry is one application that can effectively use signal processing techniques to provide caregivers with improved physiological measurements. Pulse oximetry is a widely accepted noninvasive procedure for measuring the oxygen saturation level of arterial blood, an indicator of oxygen supply. Early detection of low blood oxygen is critical in the medical field, for example in critical care and surgical applications, because an insufficient supply of oxygen can result in brain damage and death in a matter of minutes. Pulse oximeter systems are described in detail in U.S. Pat. No. 5,632,272, U.S. Pat. No. 5,769,785, and U.S. Pat. No. 6,002,952, which are assigned to the assignee of the present invention and which are incorporated by reference herein.

Figure 9:
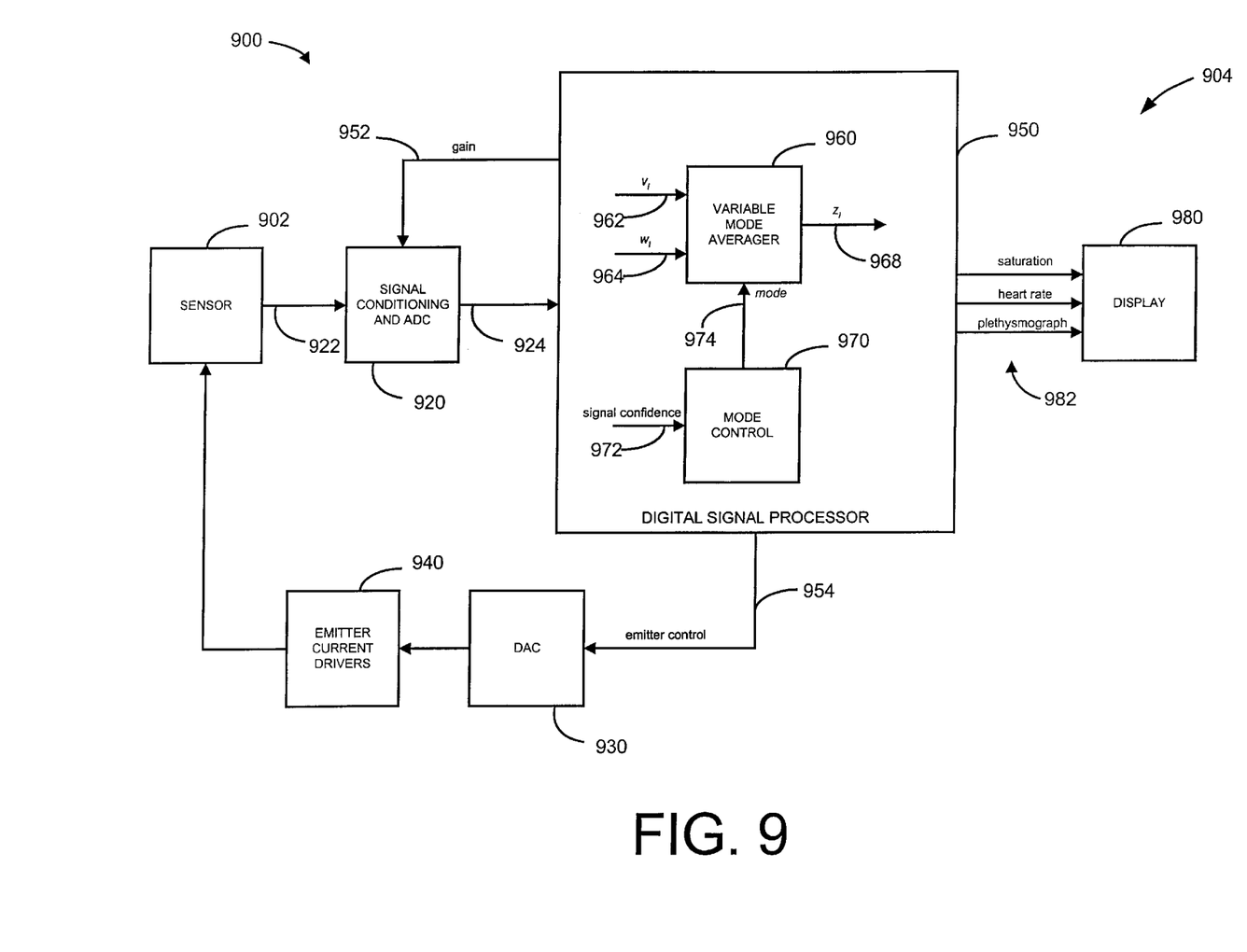
FIG. 9 is a block diagram illustrating a variable mode averager applied to a pulse oximeter.

FIG. 9 depicts a general block diagram of a pulse oximetry system 900 utilizing a variable mode averager 960. A pulse oximetry system 900 consists of a sensor 902 attached to a patient and a monitor 904 that outputs desired parameters 982 to a display 980, including blood oxygen saturation, heart rate and a plethysmographic waveform. Conventionally, a pulse oximetry sensor 902 has both red (RED) and infrared (IR) light-emitting diode (LED) emitters (not shown) and a photodiode detector (not shown). The sensor 902 is typically attached to a patient's finger or toe, or to a very young patient's foot. For a finger, the sensor 902 is configured so that the emitters project light through the fingernail and into the blood vessels and capillaries underneath. The photodiode is positioned at the fingertip opposite the fingernail so as to detect the LED transmitted light as it emerges from the finger tissues, producing a sensor output 922 that indicates arterial blood absorption of the red and infrared LED wavelengths.

As shown in FIG. 9, the sensor output 922 is coupled to analog signal conditioning and an analog-to-digital conversion (ADC) circuit 920. The signal conditioning filters and amplifies the analog sensor output 922, and the ADC provides discrete signal values to the digital signal processor 950. The signal processor 950 provides a gain control 952 to amplifiers in the signal conditioning circuit 920. The signal processor 950 also provides an emitter control 954 to a digital-to-analog conversion (DAC) circuit 930. The DAC 930 provides control signals for the emitter current drivers 940. The emitter drivers 940 couple to the red and infrared LEDs in the sensor 902. In this manner, the signal processor 950 can alternately activate the sensor LED emitters and read the resulting output 922 generated by the photodiode detector.

The digital signal processor 950 determines oxygen saturation by computing the differential absorption by arterial blood of the red and infrared wavelengths emitted by the sensor 902. Specifically, the ADC 920 provides the processor 950 with a digitized input 924 derived from the sensor output 922. Based on this input 924, the processor 950 calculates ratios of detected red and infrared intensities. Oxygen saturation values, $v_i$, are empirically determined based on the calculated red and infrared ratios. These values are an input signal 962 to the variable mode averager 960. Each of the input values, $v_i$, are associated with weights, $w_i$, which form a second input 964 to the averager 960. The individual weights, $w_i$, are indicative of the confidence in particular ones of the corresponding saturation values, $v_i$. A third input 974 sets the mode of the averager 960. The variable mode averager 960 processes the values, $v_i$, weights, $w_i$, and mode as described above with respect to FIGS. 7–8 to generate values, $z_i$. The values $z_i$ are the averager output 968, from which is derived the saturation output 982 to the display 980.

The mode signal may be generated by an external source (not shown) or it may be generated by another function within the digital signal processor. For example, mode may be generated from the confidence level of the input signal as illustrated in FIG. 9. FIG. 9 illustrates a signal confidence input 972 to a mode control process 970. The mode control process 970 maps the signal confidence input 972 to the mode input 974 of the variable mode averager 960. When the signal confidence is low, the mode control 970 sets mode to a relatively small value. Depending on the application, mode may be set close to zero. When the signal confidence is high, the mode control 970 sets mode to a relatively large value. Some applications may prefer a mode of one for a high signal confidence, but this is not a requirement. When the signal confidence is neither high nor low, mode is set to an intermediate value (in some applications, mode may be set to a value between zero and one) empirically to achieve a reasonable tradeoff between a fast saturation output response and saturation accuracy.

The signal quality of pulse oximetry measurements is adversely affected by patients with low perfusion of blood, causing a relatively small detected signal, ambient noise, and artifacts caused by patient motion. The signal confidence input 972 is an indication of the useful range of the pulse oximetry algorithms used by the digital signal processor 950 as a function of signal quality. This useful range is extended by signal extraction techniques that reduce the effects of patient motion, as described in U.S. Pat. No. 5,632,272, U.S. Pat. No. 5,769,785, and U.S. Pat. No. 6,002,952, referenced above. Signal confidence is a function of how well the sensor signal matches pulse oximetry algorithm signal models. For example, the red and infrared signals should be highly correlated and the pulse shapes in the pulsatile red and infrared signals should conform to the shape of physiological pulses, as described in U.S. patent application Ser. No. 09/471,510 filed Dec. 23, 1999, entitled *Plethysmograph Pulse Recognition Processor*, which is assigned to the assignee of the present invention and which is incorporated by reference herein. As a particular example, signal confidence can be determined by measuring pulse rate and signal strength. If the measured signal strength is within an expected range for the measured pulse rate, then the confidence level will be high. On the other hand, if the measured signal strength is outside the expected range (e.g., too high for the measured pulse rate), then the confidence level will be low. Other measured or calculated parameters can be advantageously used to set the confidence level.

Figure 10:
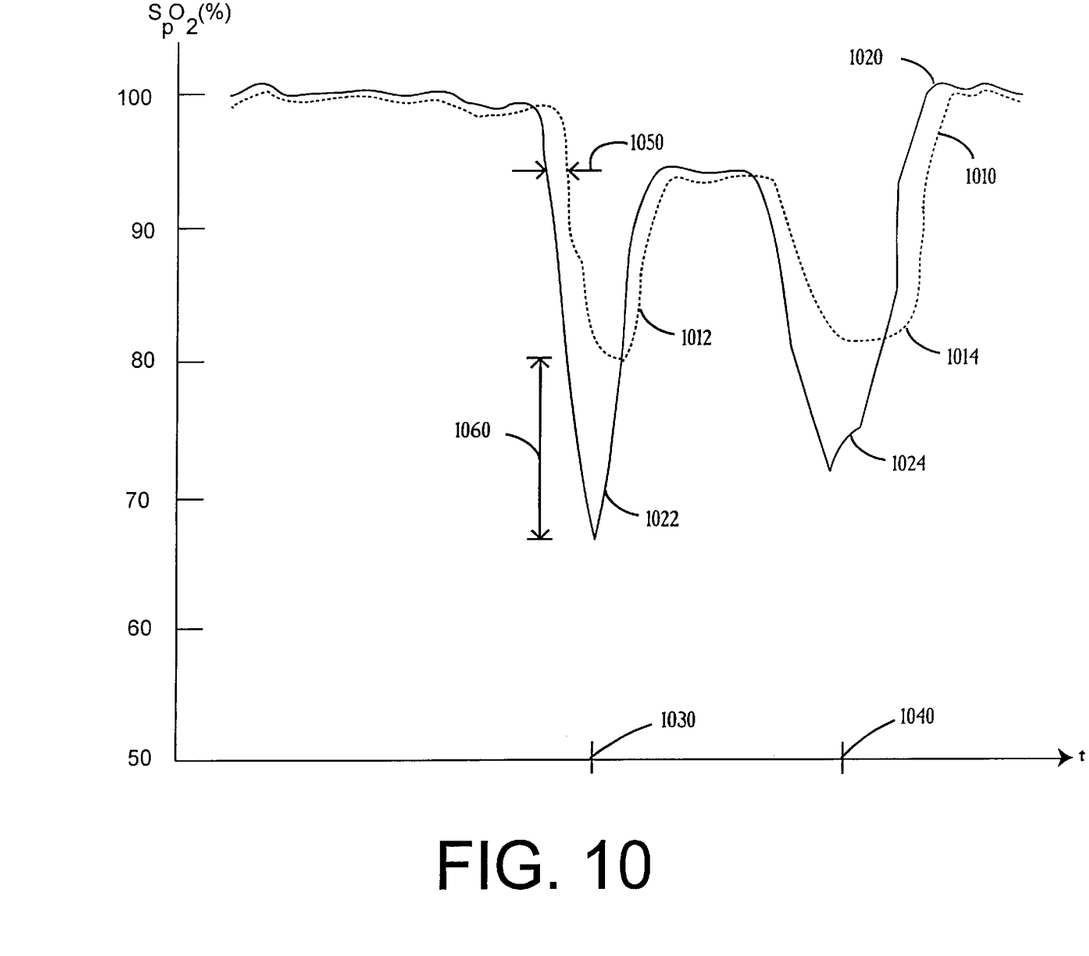
FIG. 10 is an oxygen saturation output versus time graph for a pulse oximeter utilizing a variable mode averager.

FIG. 10 illustrates the oxygen saturation output of a pulse oximeter utilizing a variable mode averager, as described above with respect to FIG. 9. A first output 1010 illustrates oxygen saturation versus time for input oxygen saturation values processed by a conventional weighted averager or, equivalently, by a variable mode averager 960 with mode≈0. A second output 1020 illustrates oxygen saturation versus time for the variable mode averager 960 with mode≈1. Each output 1010, 1020 indicates exemplary desaturation events occurring around a first time 1030 and a second time 1040. The desaturation events correspond to a patient experiencing a potentially critical oxygen supply shortage due to a myriad of possible physiological problems. With mode≈1, the variable mode averager responds to the onset of the desaturation events with less lag time 1050 than that of the conventional weighted average. Further, the variable mode averager responds to the full extent of the desaturations 1060 whereas the conventional weighted average does not. When signal confidence is low, the variable mode averager is adjusted to provide similar smoothing features to those of a conventional weighted average. When signal confidence is high, however, the variable mode averager is advantageously adjusted to respond faster and more accurately to a critical physiological event. The fast response advantage of the variable mode averager has other physiological measurement applications, such as blood-pressure monitoring and ECG.

The variable mode averager has been disclosed in detail in connection with various embodiments of the present invention. These embodiments are disclosed by way of examples only and are not to limit the scope of the present invention, which is defined by the claims that follow. One of ordinary skill in the art will appreciate many variations and modifications within the scope of this invention.

What is claimed is:

1. A variable mode averager comprising:
   a buffer that stores a plurality of weighted input values;
   a mode input that specifies a time value relative to said input values; and
   a processor coupled to said buffer, said processor configured to provide an estimate of said input values, said estimate corresponding to said time value.

2. The variable mode averager of claim 1 wherein said mode input is adjustable so that said estimate varies between that of a smoother and a forward predictor of said input values.

3. The variable mode averager of claim 1 wherein said mode input is adjustable so that said estimate varies between that of a smoother and a filter of said input values.

4. The variable mode averager of claim 1 wherein said mode input is adjustable so that said estimate varies between that of an average of said input values and a filter of said input values.

5. The variable mode averager of claim 1 wherein said mode input is adjustable based upon a characteristic associated with said input values.

6. The variable mode averager of claim 5 wherein said characteristic is a confidence level.

7. The variable mode averager of claim 6 wherein said estimate is that of a smoother when said confidence level is low and that of a filter when said confidence level is high.

8. The variable mode averager of claim 1 wherein said estimate occurs along a curve-fit of said input values at said time value.

9. The variable mode averager of claim 8 wherein said curve-fit is a linear LMS fit of said input values.

10. A signal averaging method comprising the steps of:
    identifying a plurality of signal values;
    determining a plurality of weights corresponding to said signal values;

computing a trend of said signal values adjusted by said weights;

specifying a time value relative to said signal values based upon a characteristic associated with said signal values; and estimating said signal values based upon said trend evaluated at said time value.

11. The signal averaging method of claim 10 further comprising the steps of:

determining a confidence level associated with said signal values; and specifying said time value based upon said confidence level.

12. The signal averaging method of claim 11 wherein said trend is a linear LMS fit to said signal values adjusted by said weights.

13. The signal averaging method of claim 12 wherein said time value generally corresponds to the maximum time of said signal values when said confidence level is high and said time value generally corresponds to the weighted average time of said signal values when said confidence level is low.

14. A signal averaging method comprising the steps of:

providing an input signal;

setting a mode between a first mode value and a second mode value; and generating an output signal from an estimate of said input signal as a function of said mode, wherein said output signal generally smoothes said input signal when said mode is proximate said first mode value and said output signal generally tracks said input signal when said mode is proximate said second mode value.

15. The signal averaging method of claim 14 further comprising the step of determining a characteristic of said input signal, wherein said setting step is a function of said characteristic.

16. The signal averaging method of claim 15 wherein said characteristic is a confidence level relating to said input signal.

17. The signal averaging method of claim 16 wherein said setting step comprises the substeps of:

setting said mode proximate said first mode value when said confidence level is low; and setting said mode proximate said second mode value when said confidence level is high.

18. The signal averaging method of claim 14 wherein said input signal is a physiological measurement and said setting step comprises setting said mode proximate said first mode value when said measurement is corrupted with noise or signal artifacts, otherwise setting said mode proximate said second mode value so that said output signal has a fast response to physiological events.

19. A signal averager comprising:

an input means for storing a plurality of signal values;

an adjustment means for modifying said signal values with a plurality of corresponding weights;

a curve fitting means for determining a trend of said signal values;

an estimate means for generating an output value along said trend; and a mode means coupled to said estimate means for variably determining a time value at which to generate said output value.

* * * * *